Figure 1:
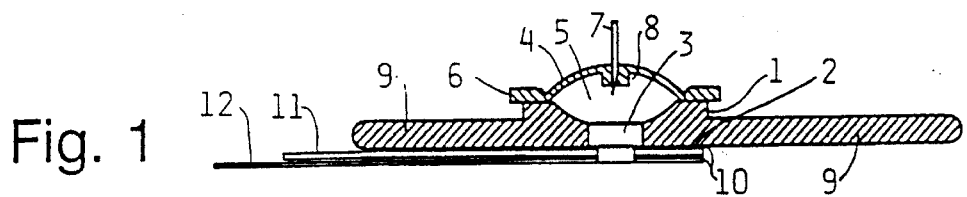

United States Patent [19]
Keljmann et al.

[11] Patent Number: 5,505,212
[45] Date of Patent: Apr. 9, 1996

[54] BLOOD SAMPLER

[75] Inventors: Troels Keljmann, Copenhagen; Peter Klitgaard, Lyngby, both of Denmark

[73] Assignee: Novo Nordisk A/S, Bagsvaerd, Denmark

[21] Appl. No.: 356,029

[22] Filed: Dec. 14, 1994

Related U.S. Application Data

[63] Continuation of Ser. No. 170,301, filed as PCT/DK92/00191, Jun. 19, 1992, abandoned.

[30] Foreign Application Priority Data

Jun. 21, 1991 [DK] Denmark ................. 1209/91

[51] Int. Cl.$^6$ ............................. A61B 5/14
[52] U.S. Cl. ................ 128/771; 128/760; 128/764; 128/767
[58] Field of Search ................ 128/760–771; 606/181–182

[56] References Cited

U.S. PATENT DOCUMENTS

| | | | |
|---|---|---|---|
| 1,960,889 | 5/1934 | Benedict | 606/181 X |
| 5,014,718 | 5/1991 | Mitchen | 606/181 X |
| 5,029,583 | 7/1991 | Meserol et al. | 606/182 X |
| 5,036,861 | 8/1991 | Sembrowich et al. | 128/760 |
| 5,054,499 | 10/1991 | Swierczek | 128/770 |
| 5,070,886 | 12/1991 | Mitchen et al. | 128/771 |
| 5,217,480 | 6/1993 | Haber et al. | 606/182 |
| 5,231,993 | 8/1993 | Haber et al. | 606/181 X |

FOREIGN PATENT DOCUMENTS

| | | |
|---|---|---|
| 0164148 | 12/1985 | European Pat. Off. |
| 3515420 | 10/1986 | Germany |
| WO85/04089 | 9/1985 | WIPO |
| WO88/06427 | 9/1988 | WIPO |
| WO92/02175 | 2/1992 | WIPO |

Primary Examiner—Sam Rimell
Attorney, Agent, or Firm—Steve T. Zelson; James J. Harrington

[57] ABSTRACT

A blood sampler comprises a small chamber having a stiletto mounted air-tightly through a flexible top wall with a pointed end of the stiletto positioned inside the chamber opposite an opening in the bottom part of the chamber. The sampler is designed to be mounted in a tool which compresses the chamber by pressing the flexible top wall against the bottom of the chamber. Further, the tool has means for imparting an impact on a blunt outer end of the stiletto to drive the stiletto further through the top wall to make its sharp end protrude through the opening in the bottom part into the skin to which the sampler may be attached by an adhesive. When the sampler is ejected from the tool, it regains its original shape, providing in the chamber a vacuum for sucking blood from the perforated skin into this chamber.

9 Claims, 1 Drawing Sheet

U.S. Patent    Apr. 9, 1996    5,505,212

BLOOD SAMPLER

This application is a continuation application of application Ser. No. 08/170,301, filed Feb. 17, 1994, now abandoned, the contents of which are incorporated herein by reference.

The invention concerns a blood sampler for taking out small blood samples of the dimension a drop or so.

For many medical purposes it is necessary to take out small blood samples to determine different blood parameters such as glucose concentration, coagulation time etc. For this purpose the skin of the patient is pierced by a stiletto to provide a small wound from which a single drop of blood is made to bleed out. The blood drop may e.g. be placed on a piece of indicator paper directly as it is often the case when the patient himself frequently makes the necessary determination of one of his blood parameters.

However, such measurement will often be made using electrochemically functioning apparatus having a sensor on which the blood drop must be placed. Such apparatus may be owned by the patient himself, but will usually be clinical equipment used in a hospital or a doctor's office for measuring of blood samples from many different patients. Unless the sensor on which the blood is to be placed is a disposable device which is disposed of each time a patient has placed his droplet of blood thereon the risk of dissimination exists when a patient is directly placing his open wounded finger with the blood drop on a sensor contaminated by blood from a previous patient.

This problem may be solved by using a disposable device for carrying the blood from the patient to the sensor. Such a device may be a small sponge into which the blood drop is absorbed and thereafter given off by squeezing the sponge at the sensor. This eliminates the risk as to the patient, but the handling of the free drop of blood on the patient's finger still presents a risk to the members of the clinic staff, especially when they have to help the patients by squeezing a pricked finger to make the blood flow or by wiping off excessive blood from the pricked finger.

The finger pricking may be performed by using a disposable lancet unit in a tool as described in Danish patent application Ser. No. 2316/90.

It is the object of the invention to provide a blood sampler by which the finger pricking and the absorption of the blood drop is obtained by using only one disposable article, and by which the risk of infecting other patients or members of the staff is minimized.

This is obtained by a blood sampler which according to the invention is characterized in that it comprises a small chamber having a stiletto mounted air tight through a flexible top wall with a pointed end of the stiletto positioned inside the chamber opposite an opening in a bottom part of this chamber, through which opening the stiletto may pass when an axial impact driving it further through the top wall of the chamber is imparted on its blunt outer end, the outer side of the bottom part forming a plane surface around the opening.

The stiletto may be shaped as a hypodermic needle having a bore, the upper end of which is closed to prevent blood from passing through the needle to the outer side of the chamber. It is experienced by some patients that pricking with a hypodermic needle is less painful than pricking with a solid stiletto.

According to the invention, the blood sampler may have means to releasably secure it in a tool deforming the flexible top of the chamber sufficiently to expel most of the air in the chamber and to bring the pointed end of the stiletto close to the opening on the inner side of the bottom part of the chamber.

Thereafter the sampler held in the tool is pressed against the skin at the sampling spot of the patient. An adhesive may be provided on the plane outer surface around the opening in the bottom part to ensure an air-tight bonding to the skin and to keep the sampler secured to the skin during the filling when the finger around the sampler is manipulated to pump blood into the sampler.

An impact is then by the tool imparted on the blunt outer end of the stiletto projecting from the top of the chamber. This impact will drive the stiletto through the top wall of the chamber and make its pointed end shoot out through the opening in the bottom part piercing the skin of the patient.

When the impact is over the sampler is expelled from the tool and the resiliency of the top wall of the chamber will make this wall return to its original position. Thereby a vacuum is provided in the chamber, which vacuum will help the blood flow into the chamber from the wound provided by the stiletto, and even if it should be necessary to help by squeezing the tissue around the sampling spot the risk of getting into contact with the blood will be eliminated. At the same time the stiletto is retracted to the inside of the chamber.

Reuse of the sampler is precluded as the stiletto has been driven through the top wall to a position in which it will project through the opening in the bottom part if the sampler is mounted in the tool. Further reuse is prevented by the adhesive being removed from the sampler as will be explained below.

According to the invention, the chamber may have at its bottom elongated non-adhesive flaps extending from diametrically opposite sides of the adhesive part around the opening. These flaps may be used for handling the sampler when placing it on the spot requested. In a preferred embodiment a plaster congruent with one of the elongated flaps at its one end surrounds the opening and is embedded in the adhesive surrounding the opening. The plaster may be covered by a protective strip which is bonded to the adhesive by a force less than the force by which the adhesive is bonded to the bottom of the sampler. When the sampler is to be used this protective strip may be removed to lay open the adhesive by which the sampler may be bonded air-tightly to the sampling spot.

By using an adhesive which bonds better to the skin of a patient than to the sampler, it is ensured that the sampler with the blood sample may be removed leaving the adhesive with the plaster on the sampling spot which may then be covered by folding the plaster to make its free strip be bonded to the adhesive previously bonding to the sampler.

The sampler may be used to transport the blood from the patient to a measuring device at which device the blood may be expelled through the bottom opening of the sampler by pressing the flexible top wall. Another possibility is that the chamber contains a sensor transforming the parameter to be measured to an electric signal which may be led out to terminals on the elongated flaps. The sampler may then be inserted with its elongated flaps in an apparatus reading out the signal.

In a more simple embodiment, an indicator may be coated on or in other way be placed at the inner side of an transparent top wall.

By these embodiments it is ensured that the measurements may be made without making the blood leave the sampler.

Figure 2:
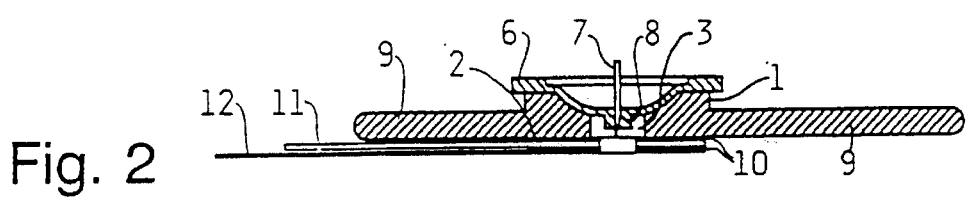
Figure 3:
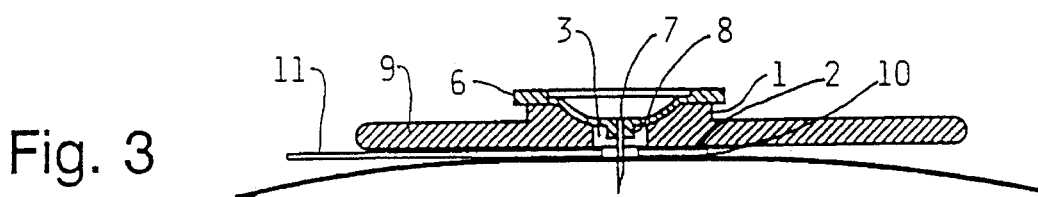
Figure 4:
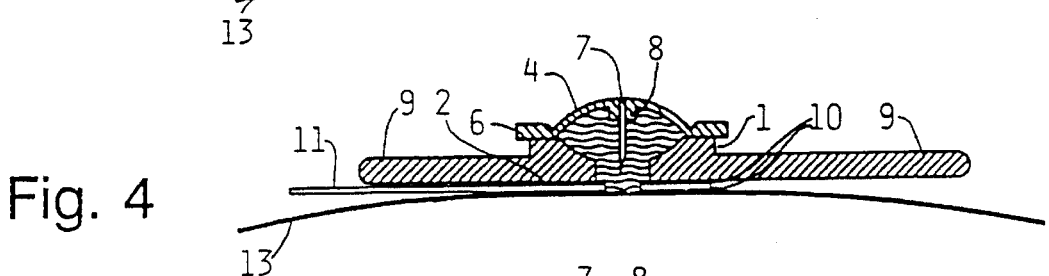
Figure 5:
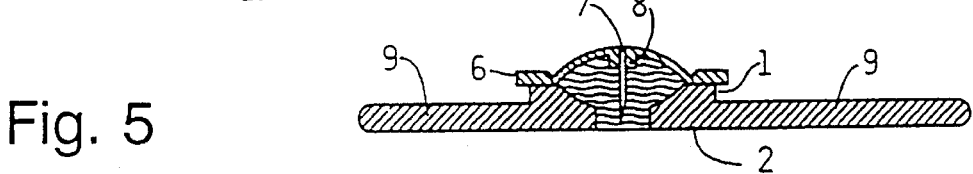
Figure 6:
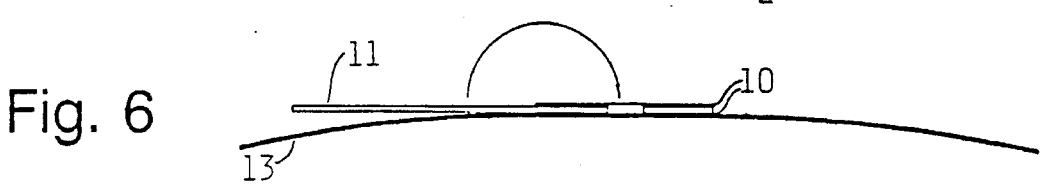
Figure 7:
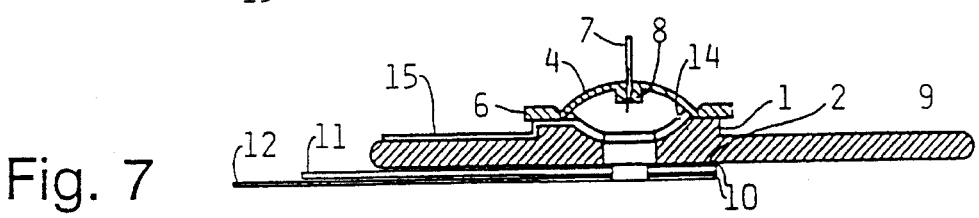
Figure 8:
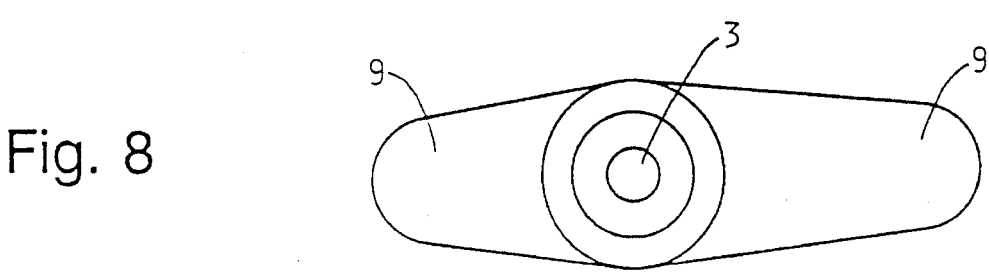

The invention will now be described in further details referring to the drawing in which FIG. 1 shows a sectional view of a sampler as it is before use, FIG. 2 shows the sampler when placed in a tool for deforming the chamber, FIG. 3 shows the sampler after the stiletto has received an impact on its blunt end to drive it into the skin of a patient, FIG. 4 shows the sampler when released from the tool and filled with blood, FIG. 5 shows the blood filled sampler removed from the sampling spot, FIG. 6 shows the adhesive with the plaster left on the skin when the sampler is removed, FIG. 7 shows a sampler as the one described, but having a built-in sensor, and FIG. 8 shows a plan view of the bottom part of the sampler in FIGS. 1–5.

The sampler in FIG. 1 comprises a circular lower part 1 having at its lower side a plane surface 2 surrounding a central opening 3 and having at its upper side a cavity, which together with an arched cavity of an upper dome shaped part 4 forms a bubble shaped chamber 5, the dome shaped upper part being bonded air-tightly with its lower edge to the upper edge of the lower part. At the lower edge the upper dome shaped part further has a circumferential projection 6 forming a ring having a diameter exceeding the diameter of the lower part. This ring projecting over the side walls of the circular lower part 1 provides an edge which may engage a socket in a not shown tool for deforming the dome shaped part 4 and for impacting an outer blunt end of a stiletto 7 mounted in a thickening 8 of the wall of the apex of the dome shaped part 4.

Extending from diametrically opposite sides of the lower part 1 integral with this lower part a pair of flaps 9 are provided having their lower surfaces flush with the plane lower surface 2 of the lower part 1.

Around the opening 3 on the plane surface 2 is provided an adhesive 10, in which an end of a medical plaster 11 is embedded, this plaster 11 being covered by a protecting strip 12 bonded with its one end by the adhesive 10.

FIG. 2 shows how the bubble is deformed when placed in a not shown apparatus or tool. The dome shaped upper part is depressed, so that its arched inner side is pressed against the surface of the cavity on the upper side of the lower part 1. The thickening 8 with the stiletto 7 is pressed into the opening 3, the stiletto being perpendicular to the plane surface 2 and extending mainly upwards from the upper side of the upper part and only a short distance into the opening 8, so that it does not project over the surface 2.

By removing the protecting strip 12 the adhesive is laid open and the sampler is bonded to the skin 13 of the patient on the spot where the sample is to be taken, whereafter the upper blunt end of the stiletto 7 is impacted by a hammer mechanism in the tool (not shown). Thereby the stiletto is driven further through the thickening 8 and into the skin 13 as shown in FIG. 3.

At the end of the hammering action of the tool the sampler is released from the tool and the deformed upper part due to its resiliency will return to its dome shape providing in the inner of the bubble a vacuum which helps to suck out blood through the wound made by the stiletto 7. The bleeding may be assisted by pressing the skin around the sampling spot which may be done without risk of coming into contact with the blood confined in the bubble. FIG. 4 shows the bubble in its blood filled condition.

When filled with blood the sampler may be removed from the samling spot. By choosing an adhesive bonding better to skin than to the material of the sampler it is ensured that the adhesive with the plaster 11 keeps sticking to the skin. Hereafter the sampler will appear as shown in FIG. 5. The plaster may then be flipped over and bonded to the adhesive as indicated by the arrow in FIG. 6.

The blood stored in the sampler may be deposited on a sensor of a measuring apparatus by holding the sampler in the flaps 9 and pressing the dome shaped part 4 by a finger.

In the embodiment shown in FIG. 7 an electrochemical sensor 14 is coated on the inner surface of the bottom part of the chamber. The electric signal provided by the sensor when the chamber is filled with blood is led through the wall by terminals 15 ending on the flaps where they may be engaged by contacts in a read-out device.

In a not shown embodiment an indicator may be coated on the top wall of the chamber or it may be placed close to this wall which should be transparent. A transparent upper wall is also preferred in embodiments not having the built-in sensor 2 as such a transparent wall 2 allows inspection of the filling of the sampler.

We claim:

1. A blood sampler comprising a chamber having flexible top wall with an inner and an outer side, a bottom part with an inner and an outer side whereof the outer side forms a plane surface and a bottom part includes an opening, a stiletto having a blunt end and a pointed end, which stiletto slidably is mounted in an air tight relationship with the top wall and wherein the stiletto is driven through this top wall when an impact is imparted on the blunt end of this stiletto and the stiletto is mounted so that the pointed end does not project far enough from the inner side of the top wall to pass through the opening in the bottom part when the top wall is pressed against the inner side of the bottom part.

2. A blood sampler according to claim 1, wherein the stiletto is shaped as a hypodermic needle having a bore an upper end of which is closed.

3. A blood sampler according to claim 1, wherein an adhesive is provided on a part of the plane surface around the opening.

4. A blood sampler according to claim 3, wherein the chamber has at its bottom elongated non-adhesive strips extending from opposite sides of the chamber.

5. A blood sampler according to claim 4, wherein a plaster congruent with one of the elongated strips has an end surrounding the opening and being embedded in the adhesive surrounding the opening.

6. A blood sampler according to claim 5, wherein a protective strip covers the plaster and is bonded to the adhesive by a force less than the force by which the adhesive is bonded to the bottom of the chamber.

7. A blood sampler according to claim 1, wherein measuring means are mounted in the chamber.

8. A blood sampler according to claim 7, wherein the measuring means are a sensor transforming a parameter to be measured into an electric signal, which is led to terminals outside the chamber.

9. A blood sampler according to claim 8, wherein the measuring means are an indicator at the inner side of a transparent wall.

* * * * *